(12) United States Patent
Berger et al.

(10) Patent No.: US 8,273,909 B2
(45) Date of Patent: Sep. 25, 2012

(54) PROCESS FOR PREPARING COMPLEXES OF PALLADIUM (HYDROGEN)CARBONATE WITH AMINE LIGANDS

(75) Inventors: Sascha Berger, Schwaebisch Gmuend (DE); Franz Simon, Schwaebisch Gmuend (DE); Frank Oberst, Schwaebisch Gmuend (DE); Uwe Manz, Moegglingen (DE); Klaus Bronder, Schwaebisch Gmuend (DE); Bernd Weyhmueller, Alfdorf Hintersteinenberg (DE)

(73) Assignee: Umicore Galvanotechnik GmbH, Schwaebisch Gmuend (DE)

( * ) Notice: Subject to any disclaimer, the term of this patent is extended or adjusted under 35 U.S.C. 154(b) by 155 days.

(21) Appl. No.: 12/991,214

(22) PCT Filed: May 7, 2009

(86) PCT No.: PCT/EP2009/003251
§ 371 (c)(1),
(2), (4) Date: Nov. 5, 2010

(87) PCT Pub. No.: WO2009/135668
PCT Pub. Date: Nov. 12, 2009

(65) Prior Publication Data
US 2011/0060154 A1    Mar. 10, 2011

(30) Foreign Application Priority Data

May 7, 2008    (EP) ...................................... 08008573

(51) Int. Cl.
$C07F\ 15/00$    (2006.01)
(52) U.S. Cl. ...................................................... 556/137
(58) Field of Classification Search .................. 556/137
See application file for complete search history.

(56) References Cited

U.S. PATENT DOCUMENTS
6,743,346 B2    6/2004    Gonzalez et al.

FOREIGN PATENT DOCUMENTS
WO    2007/029031    3/2007

*Primary Examiner* — Porfirio Nazario Gonzalez
(74) *Attorney, Agent, or Firm* — Smith, Gambrell & Russell, LLP

(57) ABSTRACT

The present invention relates to a process for preparing palladium complexes. In particular, the present invention relates to a process in which ammoniacal complexes of palladium (hydrogen)carbonate are converted into complexes with oligoamine ligands.

8 Claims, No Drawings

PROCESS FOR PREPARING COMPLEXES OF PALLADIUM (HYDROGEN)CARBONATE WITH AMINE LIGANDS

The present invention relates to a process for preparing palladium complexes. In particular, the present invention relates to a process in which ammoniacal complexes of palladium (hydrogen)carbonate are converted into complexes with amines.

Conventional palladium-nickel electrolytes contain ammonia and chloride and are therefore a potential hazard to the health of operating personnel and are damaging in terms of the corrosion of the plant material. The conventional alkaline-ammoniacal processes according to the prior art use tetraamminepalladium(II) chloride [$(NH_3)_4Pd]Cl_2$ or diamminepalladium(II) dinitrite [$(NH_3)_2Pd](NO_2)_2$ as palladium compound for the deposition of palladium or a palladium alloy. In existing chloride-free processes, tetraamminepalladium(II) sulfate [$(NH_3)_4Pd]SO_4$ is used in place of the chloride compound (Galvanotechnik 3 (2007), p. 677). In these processes, the corrosive chloride is dispensed with, i.e. attack on the plant material is significantly reduced as a result. However, the hazard to the health of human beings due to ammonia vapors given off remains.

As early as 1986, Raub and Walz described the electrochemical deposition of palladium-nickel coatings from an electrolyte based on ethylenediamine (Metalloberfläche 40 (1986) 5, p. 199-203, D. Walz and Ch. J. Raub, "Die galvanische Palladium-Nickel-Abscheidung aus ammoniakfreien Grundelektrolyten mit Ethylendiamin als Komplexbildner"). It is explained in this paper that the complexing agent ethylenediamine is ideal for moving the deposition potentials of the two metals sufficiently close together for deposition of an alloy to be possible. In this electrolyte, [$Pd(EDA)_2$]X was used as palladium complex (X=anion(s)). Chloride, bromide, sulfate and sulfamate were used as anions.

A process known from US patent (U.S. Pat. No. 6,743,346) also uses ethylenediamine as complexing agent and introduces the palladium in the form of the solid compound of palladium sulfate and ethylenediamine. The salt contains from 31 to 41% of palladium (molar ratios of [$SO_4$]:[Pd] from 0.9 to 1.15 and [ethylenediamine]:[Pd] from 0.8 to 1.2). It is not soluble in water but dissolves in the electrolyte in the presence of an excess of ethylenediamine. Although the salt makes it possible to introduce palladium with a reduced amount of ethylenediamine, the increased sulfate content leads to an increased level of salts in the electrolyte and thus to shortening of the lifetime of the bath.

In the preparation of the tetraamminepalladium(II) halides or tetraamminepalladium(II) sulfate, the corresponding simple palladium salts such as palladium(II) chloride or bromide or iodide or palladium(II) sulfate are used as starting materials and these are reacted with 4 parts of ammonia. This forms the water-soluble complexes [$(NH_3)_4Pd]X_2$ where X=Cl, Br, I or [$(NH_3)_4Pd]SO_4$. The analogous hydrogencarbonate [$Pd(EDA)_2](HCO_3)_2$ can at present not be prepared by this synthetic route since a corresponding Pd(II) dihydrogencarbonate $Pd(HCO_3)_2$ does not exist or is not commercially available. The situation is similar for the corresponding carbonate salt.

It was therefore an object of the present invention to provide a process for preparing complexes of palladium(II)carbonate or hydrogencarbonate with amine ligands. This should allow the desired compounds to be prepared in an ecologically or economically advantageous manner in a simple process.

This object is achieved as described in the claims.

A process for preparing palladium complexes comprising a divalent palladium cation, one or more amine ligands and a carbonate anion or two hydrogencarbonate anions or a mixture thereof in which the corresponding tetraamminepalladium(II) dihydrogencarbonate or tetraamminepalladium(II) carbonate is reacted in solution with the amine ligand under conditions under which the ammonia liberated can be removed, completely surprisingly but nonetheless advantageously leads to achievement of the stated object. The process allows the desired compounds to be prepared in high yields and extremely high purity, so that they can be used for electrochemical deposition of palladium with the advantages outlined.

In principle, a person skilled in the art can make a free choice of the amine ligands to be used. The choice will be guided by the ligands which are available and can easily be obtained commercially or preparatively. It is advantageous to use one or more bidentate, tridentate or tetradentate ligands, e.g. ligands based on diamines, triamines or tetraamines. Particular preference is given to those having from 2 to 11 carbon atoms. Very particular preference is given to using ligands selected from the group consisting of ethylenediamine, trimethylenediamine, tetramethylenediamine, pentamethylenediamine, hexamethylenediamine, 1,2-propylenediamine, trimethylenetetramine, hexamethylenetetramine. Especial preference is given to ethylenediamine (EDA) in this context.

Depending on whether the amine ligand is a monodentate or polydentate ligand, the amine ligands are used in a different stoichiometric ratio to the tetraamminepalladium(II) salt. The tetraamminepalladium(II) salt is preferably reacted in a molar ratio of 1:1.0-4.5, preferably 1:1.0-3.0, particularly preferably 1:1.0-2.5, with the amine ligand. In the case of bidentate ligands, in particular ethylenediamine, the ratio is 1:1.0-3.0, preferably 1:1.5-2.5, particularly preferably 1:2.0-2.1.

The temperature in the reaction can be chosen freely by a person skilled in the art. The choice will be guided by the desirability of achieving a very complete conversion with preferably total suppression of secondary reactions. The temperature during the reaction is preferably from 20° C. to 100° C. The temperature is particularly preferably from 40 to 90° C., very particularly preferably from 60 to 80° C.

To complete the removal of the ammonia from the complex in question, a person skilled in the art will choose measures which are available for this purpose. Application of a vacuum during the ligand exchange appears to be advantageous. As a result, the reaction is pulled in one direction by the continual disturbance of the equilibrium. The embodiment in which the ammonia formed is additionally driven out of the solution by passing in an inert gas has likewise been found to be advantageous. Both measures help to remove ammonia from the equilibrium and allow the temperature being employed during the reaction to be reduced while still obtaining a sufficient reaction rate.

The reaction according to the invention can be carried out in all solvents considered suitable by those skilled in the art. These are preferably solvents which are inert in respect of the reaction but dissolve the materials in question to a sufficient extent. For example, it is possible to use aqueous solutions. These comprise more than 50% by weight of water in addition to water-soluble organic solvents. Preference is given to using exclusively water as solvent. The pH of the solution is set so that ammonia can be removed from the reaction mixture. The pH is advantageously in the alkaline range. Preference is given to a range of 7-14, more preferably 8-13 and particularly preferably 9-12. Especial preference is given to the pH being 9-11, in particular for the preparation of the corresponding hydrogencarbonate salt.

A person skilled in the art can choose the order of addition of the reactants. However, in a preferred embodiment, the amine ligand is initially charged in the solution and the tetraamminepalladium(II) salt is subsequently added.

For example, the preparation of a palladium-ethylenediamine compound can be carried out by reacting tetraamminepalladium(II) dihydrogencarbonate Alfa Aesar cat. No. 45082] with ethylenediamine. As described in the example, ethylenediamine is initially charged in water and the tetraamminepalladium(II) dihydrogencarbonate is subsequently added a little at a time with vigorous stirring. It is likewise possible to add the starting materials in the reverse order. For this purpose, the tetraamminepalladium(II) dihydrogencarbonate can, for example, be slurried in water and ethylenediamine can be added via a dropping funnel with vigorous stirring. During the subsequent reaction time of about 1 hour at up to 100° C. under reflux, the product bis(ethylenediamine)palladium(II) dihydrogencarbonate is formed.

A ligand exchange of ammonia and ethylenediamine takes place according to the following reaction equation:

[(NH$_3$)$_4$Pd](HCO$_3$)$_2$+2H$_2$N—CH$_2$—CH$_2$—NH$_2$→
[(H$_2$N—CH$_2$—CH$_2$—NH$_2$)$_2$Pd](HCO$_3$)$_2$+4NH$_3$

The ammonia liberated is partly given off immediately from the solution or is subsequently driven out by blowing in a stripping gas, e.g. air or nitrogen. To accelerate this removal of ammonia, a vacuum can additionally be applied. The solution obtained is yellow and clear and has a pH of from 9.5 to 10.

The complex can be obtained as a pure solid by evaporation of the solution or by removal of the solvent, if appropriate under reduced pressure. It can advantageously be used in this solid form or as a solution in corresponding electrolytic baths and helps to prevent an increase in the salt content of the bath when consumed palladium is replenished by addition of palladium in the form of the (hydrogen)carbonate to the bath.

EXAMPLE

Reaction of Tetraamminepalladium(II) Dihydrogencarbonate With Ethylenediamine by Ligand Exchange with Ethylenediamine (EDA)

Apparatus:
Three-necked flask, stirrer, heater, thermometer, reflux condenser, pH electrode.
Starting Materials:

| Component | Mass [g] | Molar amount [mol] | Molar mass [g/mol] | Density [g/cm$^3$] | Volume [ml] |
|---|---|---|---|---|---|
| Palladium | 100 * | 0.940 | 106.4 | — | — |
| Ethylenediamine (EDA) | 117 | 1.947 | 60.1 | 0.898 | 130 |

* 277 g of tetraamminepalladium(II) dihydrogencarbonate TAPHC (36% of Pd)
Molar ratio of Pd:EDA = 1:2.07

Quality of the Chemicals Used:
Tetraamminepalladium(II) dihydrogencarbonate (product No. 45082) from Alfa Aesar Ethylenediamine, 99%, synthetic reagent (e.g. Merck No. 800947)

Procedure for 1 liter final volume containing 100 g of Pd:
1. Place 500 ml of deionized water in a reaction vessel.
2. Add ethylenediamine to the water (pH 11.5-12).
3. Add tetraamminepalladium(II) hydrogencarbonate a little at a time; temperature rises to above 50° C. A golden yellow solution is formed. After addition of the full amount of the palladium salt, the pH is about 10.5.
4. Heat to 80° C. and allow to react for 1 h. On heating, the color of the solution changes from golden yellow to greenish yellow. Slight turbidity due to black particles is obtained.
5. Allow the mixture to cool to 50° C.
6. Filter the mixture through a No. 6 glass fiber filter: a little black residue on the filter, light-yellow solution which smells strongly of ammonia.
7. Pass compressed air through the solution to decrease the ammonia concentration.
8. Make up to the final volume with deionized water.

The invention claimed is:

1. A process for preparing palladium complexes comprising a divalent palladium cation, one or more amine ligands and a carbonate anion or two hydrogencarbonate anions or a mixture thereof, wherein the corresponding tetraamminepalladium(II) dihydrogencarbonate or tetraamminepalladium(II) carbonate is reacted in solution with the amine ligand under conditions under which the ammonia liberated can be removed.

2. The process as claimed in claim 1, wherein amine ligands selected from the group consisting of ethylenediamine, trimethylenediamine, tetramethylenediamine, pentamethylenediamine, hexamethylenediamine, 1,2-propylenediamine, trimethylenetetramine, hexamethylenetetramine.

3. The process as claimed in claim 1, wherein the tetraamminepalladium(II) salt is reacted in a molar ratio of 1:1.0-4.5 with the amine ligand.

4. The process as claimed in claim 1, wherein the temperature during the reaction is set in the range from 20° C. to 100° C.

5. The process as claimed in claim 1, wherein the process is carried out with application of a vacuum.

6. The process as claimed in claim 1, wherein the ammonia formed is additionally driven out of the solution by passing an inert gas into the solution.

7. The process as claimed in claim 1, wherein the process is carried out in an aqueous solution.

8. The process as claimed in claim 1, wherein the amine ligand is initially charged in the solution and the tetraamminepalladium(II) salt is subsequently added.

* * * * *